United States Patent [19]

Kulpa et al.

[11] Patent Number: 5,100,800
[45] Date of Patent: Mar. 31, 1992

[54] MICROORGANISM FOR DEGRADING TOXIC WASTE MATERIALS

[76] Inventors: Charles F. Kulpa, 19145 Greenacre, South Bend, Ind. 46637; Michael G. Johnston, 316 Monk Rd., Durham, N.C. 27704

[21] Appl. No.: 245,592

[22] Filed: Sep. 19, 1988

Related U.S. Application Data

[62] Division of Ser. No. 881,767, Jul. 3, 1988, Pat. No. 4,803,166.

[51] Int. Cl.$^5$ ............................................. D06M 16/00
[52] U.S. Cl. ................................... 435/264; 435/262; 435/253.3; 435/877

[58] Field of Search .................... 435/253.3, 262, 877, 435/264

[56] References Cited

PUBLICATIONS

Official Gazette of the United States Patent and Trademark Office, vol. 1123, No. 4, 1123 OG 59, 1991.

Primary Examiner—David M. Naff
Assistant Examiner—Marian C. Knode

[57] ABSTRACT

A microorganism is disclosed for degrading toxic waste materials into more environmentally acceptable materials. Processes for utilizing the microorganism in a sequencing batch reactor, and for treating industrial and municipal wastes, such as chemical waste landfill leachate and chemical process wastewater, are also disclosed.

9 Claims, No Drawings

MICROORGANISM FOR DEGRADING TOXIC WASTE MATERIALS

This is a division of application Ser. No. 881,767, filed July 3, 1986, now U.S. Pat. No. 4,803,166

BACKGROUND OF THE INVENTION

This invention relates to a new microorganism for degrading recalcitrant toxic waste materials, and particularly chlorinated aromatic compounds, into materials which are more environmentally acceptable.

The chemical industry annually generates enormous quantities of synthetic chemicals such as dielectric fluids, flame retardants, refrigerants, heat transfer fluids, lubricants, protective coatings, pesticides, including herbicides and insecticides, as well as many other chemicals and petroleum products used in agriculture, industry and health care. While these materials are invaluable and sustain a high standard of living for the population, they ar foreign to the biosphere and can cause serious problems when released into the environment. Other sources of toxic chemicals include the waste materials generated during the manufacture of such useful chemicals.

Large amounts of the toxic chemicals generated annually by the chemical industrial accumulate in animal and plant tissues and can cause serious health problems. Since these chemicals are not products of natural processes, and may possess structural features which are not commonly found in nature, they tend to persist in the environment and are resistant to degradation from naturally occurring organisms. Halogenated aromatic compounds are known to be particularly hazardous and also strongly resistant to biodegradation due to their cyclic natures and low concentration in the environment. Therefore, they tend to persist and accumulate to dangerous levels. Some of these materials are toxic, mutagenic and/or carcinogenic at very low concentration. Polychlorinated biphenols (PC's), chlorinated phenoxyacetates, and chlorinated benzoic acids (CBS's) are examples of chlorinated aromatic compounds considered to be hazardous wastes and priority pollutants. These chemicals are introduced directly into the biosphere as herbicides, pesticides, electrical transformer fluids or land treatment systems, or indirectly from unsuccessful landfills, chemical spills, or as wastes from chemical manufacturing processes, depending on their production method, shipment, use and disposable. Human exposure to and concern over these chemicals has increased in recent years due to increasing population density and industrial activity. Chlorinated benzoic acid or chlorobenzoates are of particular concern since they are intermediates in the microbial metabolism of more complex chlorinated aromatic compounds.

A variety of microorganisms have been isolated that have the capability of efficiently utilizing aromatic organic chemicals as sole carbon sources for growth (e.g. toluene, phenol, and naphthalene). See Clarke, P. H. and Oornston, L. N. (1975) "Metabolic Pathways and Regulations", 1, 191–196 in Clarke, P. H. and Richmond, M. H. (ed.), "Genetics and Biochemistry of Pseudomonas", John Wiley London. However, the corresponding chlorinated aromatic compounds (chlorotoluenes, chlorophenols, chloronaphthalenes) are biodegraded very slowly, if at all. See Alexander, M. (1973) "Non-Biodegradable and Other Recalcitrant Molecules", Biotechnology-Bioengineering, 15: 611–647.

A possible reason for this recalcitrance is the reduced reactivity of halogenated aromatic rings. The aromatic ring must be cleaved for the cycling of carbon in the metabolism of aromatic hydrocarbons. The presence of a halogen substituent on the aromatic ring adversely affects degradation. A halogen is an electronegative substituent which lowers the electron density of sites around the aromatic ring thereby reducing the chemical reactivity of the compound, rendering the ring less susceptible to microbial attack. These steric effects are influenced by the nature, position, and degree of substitution. As the number of halogen substituent increases, the arylhalide becomes less susceptible to microbial attack.

Notwithstanding, microorganisms have been isolated from the environment that are capable of growth on chlorinated aromatic compounds. For example, Chakrabarty, A. M. (1976) "Plasmids in Pseudomonas"; Ann. Rev. Genet. 10, 7–30, discloses bacteria which utilize haloaromatic compounds and the degradative pathways of intermediates involved. Several other publications deal with the microbiodegradation of halogenated hydrocarbons. For example, Bourquin, A. W. and Gibson, D. T. (1978) "Microbial Degradation of Halogenated Hydrocarbons; Water Chlorination Environmental Impact and Health Effects", 2, 253–264 disclose various microorganisms such as "Aspergillus sp., Achromoacter sp., Arthrobacter sp. and Clostridium sp., as useful for dehalogenation of various substrates such as 2-chlorophenoxyacetate, 2,4-dichlorophenol, 3-chlorobenzoate, hexachlorocyclohexane, and 4-chlorobenzoate. Gibson, D. T., Koch, J. R., Schuld, C. L. and Kallio, R. E. (1968)—Biochemistry, 7 N. 11,3795- 3802 in their paper on "Oxidative Degradation of Aromatic Hydrocarbons by Microorganisms including the Metabolism of Halogenated Aromatic Hydrocarbons," disclosed *Pseudomonas putida* as useful in the degradation of toluene and chlorinated compounds such as halobenzenes and p-chlorotoluene and state that the presence of halogen atoms greatly reduces the biodegradability of aromatic compounds. They also disclose that microorganisms have been isolated that have the capability to cometabolize a chlorinated aromatic chemical during growth on its nonchlorinated analog. For example, the conversion of chlorotoluene to chlorocatechol during growth of *Pseudomonas putida* on toluene has been demonstrated. This organism would no further metabolize the chlorocatechol, rather it is known that other microorganisms possess the ability to metabolize chlorocatechols. See Dorn, E. M., Hellwig and Reineke, W. and Knackmuss, J. H. (1974), "Isolation and Characterization of a 3-Chlorobenzoate Degrading Pseudomonas", Arch. Microbiology 99, 61–70 and also see Evans, W. C.; Smith, B. S. W.; Fernley, H. N.; and Davies, J. I, (1971), "Bacterial Metabolism of 2,4-Dichlorophenoxy Acetate, Biochem J., 122, 543–55. Chlorocatechol is known to be an intermediate in any of the metabolic pathways for utilization of chlorinated aromatic compounds. The chlorocatechol is further metabolized with the subsequent removal of chlorine. See Tiedje, J. M.; Duxbury, J. J.; Alexander, M. and Dawson, J. E. (1969), 2,4-D Co-metabolism: Pathway of Degradation of Chlorocatechols by Arthrobacter, J. Agr. Food Chem, 17, 1021–2026. Hartmann, J. Reineke, W., Knackmuss, H. J., (1979) Applied & Environmental Microbiology; 37, No. 3, 421–428 show a species of Pseudomonas identified as sp. WR 912 capable of degrading chlorobenzoic acids. Shubert, R., (1979) Fed.

Ministry for Research and Technology, Goethe University, Frankfurt, W. Germany in his paper on "Toxicity of Organohalogen Compounds", discloses the minimal inhibitory concentrations preventing growth of various bacteria including a *Pseudomonas cepacia* in various chlorinated compounds including chlorotoluene.

Cometabolism is effective in the biodegradation of haloaromatic xenobiotic compounds because they do not have to serve as a sole source of carbon and energy for the microorganisms. It allows a microbial population to eliminate the toxicity of a hazardous compound while growing on another. In addition, through a series of cometabolic reactions among different microorganisms, total degradation of a compound could occur. PCB's, chlorinated phenoxyherbicides, and chlorinated benzoic acids are all known to be degraded slowly through cometabolism.

The cometabolic theory was utilized to develop a technique termed analogue enrichment as a means of inducing microbial degradation of environmental pollutants. See Horvath, R. S. and Alexander, M. "Cometabolism of m-Chlorobenzoate by an Arthrobacter", *Applied Microbiology* 20, 254 (1970). This technique takes into account the fact that microorganisms will attack a normally non-biodegradable substance in the presence of a substrate which is similar in structure to the target compound. The analogue induces the necessary enzyme system for the degradation of the recalcitrant compound. Analogue enrichment increases the decomposition rate of the target compound.

It has been suggested that because halogenated compounds are not generally found in nature, microorganisms have not evolved which possess efficient enzyme systems or genes which express themselves for the degradation of such chemicals; see Chatterjee, D. K., Kellogg, S. T., Furukawa, K., Kilbane, J. J., Chakrabarty, A. M., "Genetic Approaches to the Problems of Toxic Chemical Pollution", Third Cleveland Symposium on Macromolecules, 1981. Chakrabarty disclosed a technique for artificially inducing the biodegradability of 2,4,5-trichlorophenyl acetic acid (2,4,5 T) by gradually exposing bacteria to increased concentrations of the chemical over the course of about one year; see Chatterjee, D. K., Kellogg, S. T., Eatkins, D. R. and Chakrabarty, A. M. in "Molecular Biology, Pathogenicity and Ecology of Bacterial Plasmids", Plenum Publishing Corp., N.Y., 1981, pp. 519-528.

U.S. Pat. Nos. 4,477,570 and 4,493,895, issued Oct. 16, 1984 and Jan. 15, 1985, respectively, the disclosures of which are incorporated by reference herein, disclose strains of *Pseudomonas cepacia* which possess the capability of biodegrading halogenated organic compounds such as chlorobenzoates and chlorotoluates. These microorganisms were isolated from soil samples obtained from a landfill site which had been used for the disposal of chlorinated organic wastes during the period 1955-1975, and are identified as ATCC 31939, ATCC 31940, ATCC 31941, ATCC 31942, ATCC 31943, ATCC 31944, and ATCC 31945, all based on deposits made at the American Type Culture Collection. The plasmids contained in these microorganisms which code for the degradation of chlorinated aromatic compounds were isolated and designated as pRO 4.7, pRO 31 ad pRO 54. Other plasmids which code for the degradation of chlorinated aromatic compounds are shown in the following Table 1:

TABLE 1

| Plasmid | Degradative Pathway |
| --- | --- |
| pAC21 | p-chlorobiphenyl |
| pAC25 | 3-chlorobenzoate |
| pAC27 | 3- and 4-chlorobenzoate |
| pAC29 | 3-, 4-, and 3,5-dichlorobenzoate |
| pJR2 | 2,4-dichlorophenoxyacetate |
| pAC31 | 3,5-dichlorobenzoate |
| pKF1 | chlorinated biphenyls |
| pJP1 | 2,4-dichlorophenoxyacetate |

The plasmids listed in Table 1 are found in such diverse microorganisms as *Pseudomonas putida*, *Pseudomonas aeruginosa*, *Kelbsiella pneumonia*, *Serratia manscescens* gram negative *Acinetobacter* and gram positive *Arthrobacter*.

The use of microorganisms for the treatment of wastewater is an economical alternative to physical treatment systems since biological treatment involves lower capital investment, lower energy requirements, a self-sustaining operation, and finally, the possibility for product recovery. In addition, biological systems offer the possibility of treatment in pre-existing municipal waste facilities, thus lowering the initial capital investment even further.

One particular biological treatment system of current interest is the sequencing batch reactor (SBR), which is a fill and draw activated sludge system operated in a batch treatment mode and utilizing a single tank for equalization, aeration and sedimentation. The use of a sequencing batch reactor with an inoculum of microorganisms capable of degrading chlorinated hydrocarbons is described in U.S. Pat. No. 4,511,657, issued Apr. 16, 1985, the disclosure of which is incorporated by reference herein.

Although several types of microorganisms which demonstrate the capacity of use chlorinated aromatic compounds as their sole source of carbon and energy are known, many of these microorganisms are not suitable for use in commercial processes for degrading these compounds due to such factors as a low growth rate in the treatment medium, insufficient metabolism of the target compound, selective nutritional preferences, and adverse competitive effects with other microorganisms. For instance, two active microorganisms described in U.S. Pat. No. 4,477,570 are *Pseudomonas cepacia* strains SS3 and H4, identified by accession numbers ATCC 31943 and ATCC 31941, respectively. Although both of these microorganisms demonstrate the capacity for metabolizing 2-chlorobenzoic acid and 4-chlorobenzoic acid, respectively, on solid growth medium, neither microorganism is capable of metabolizing these compounds in a liquid environment. This characteristic would inhibit the use of these microorganisms in biological treatment systems such as the sequencing batch reactor.

SUMMARY OF THE INVENTION

In accordance with the present invention, a novel microorganisms designated as *Pseudomonas putida* strain UNK-1 is disclosed having the capacity to utilize 2-chlorobenzoic acid as its sole source of carbon and energy in a liquid culture. This microorganism was isolated from a sequencing batch reactor culture medium bioaugmented with a microorganisms obtained from a toxic chemical landfill site and possessing a limited capability for metabolizing haloaromatic compounds.

A process for utilizing this microorganism to degrade halogenated organic chemicals contained in soils and leachate, such as by the use of a sequencing batch reactor, is also disclosed.

DETAILED DESCRIPTION OF THE INVENTION

A new microorganism has been isolated from the biomass of a sequencing batch reactor inoculated with a strain of microorganism obtained from a chemical waste landfill site designated as *Pseudomonas putida* strain SS3. Strain SS3 is also disclosed in U.S. Pat. No. 4,477,570, and has demonstrated the capability of utilizing 3-chlorotoluene as its sole source of carbon and energy. The sequencing batch reactor from which the new microorganism was isolated utilized a chemical landfill leachate feed and was operated in accordance with the general procedure described in U.S. Pat. No. 4,511,657, and as more particularly described in Example 1 below.

The new microorganism, designated as *Pseudomonas putida* strain UNK-1, has the unique characteristic of being able to degrade haloaromatic compounds, and particularly 2-chlorobenzoic acid, in a liquid medium. This enables the microorganism to be successfully used in a sequencing batch reactor as part of the stable biomass of the reactor to degrade haloaromatic compounds which are present in the reactor feed stream. In this manner, the sequencing batch reactor can be advantageously used to treat chemical landfill leachate containing recalcitrant chlorinated organics. Alternatively, the microorganism can be used directly to treat soils contaminated with such recalcitrant compounds using known techniques. This new microorganism has been deposited with In Vitro International, Inc., and assigned accession number IVI 10112 (Since the In Vitro International is no longer recognized as an international depository authority, that deposit is now being maintained by American Type Culture Collection, 12301 Parklane Drive, Rockville, Md. 20852-1776, as ATCC 68832).

A diagram of a typical sequencing batch reactor is provided in R. L. Irvine, *Journal of Water Pollution Control Federation, Vol.* 51, No. 2, pages 235-304 (1979).

As contemplated herein, the sequencing batch reactor contains an activated sludge inoculated with the microorganism of this invention. The type of activated sludge employed is not critical, and any municipal or industrial sludge may be used since it generally contains a variety of organisms capable of metabolizing organics. Activated sludge is predominantly composed of bacteria, protozoa, and fungi. Other constituents are often present such as blue-green algae, rotifers, insect larva, etc., but usually not in significant numbers. Over 300 strains of bacteria, 230 species of protozoa and 50 species of fungi have been found in various activated sludges.

The bench scale sequencing batch reactor is made of any material of construction generally employed in wastewater treatment facilities. It is usually cylindrical in shape and is equipped with air diffusers which are used for mixing and aeration. A peristaltic pump is installed in the inlet feed line to the reactor. The reactor is provided with an outlet, and solenoid valves are provided at the outlet and in the air diffuser line. Programmable timers are provided at the pumps and the agitators, if used, or air diffusers, and at the outlet line.

The SBR system may be composed of one or more such vessels, and in biological waste treatment, each tank in the system has five basic operating modes and periods, each of which is named according to its primary function. The periods are FILL, REACT, SETTLE, DRAW and IDLE, in time sequence. FILL (the receiving of raw waste) and DRAW (the discharge of treated effluent) must occur in each complete cycle for a given tank. REACT (the time to complete desired reactions), SETTLE (the time to separate the organisms from the treated effluent), and IDLE (the time after discharging the tank and before refilling) can be eliminated depending on requirements of the treatment problem. For example, if an SBR system were being used for equalization only, each cycle might only involve fill and draw.

The time for a complete cycle is the total time between beginning of fill to end of idle in a single-tank system and between beginning of fill for the first reactor (arbitrarily defined) and the end or idle for the last reactor in a multiple-tank system. In a multiple-tank system, the reactors fill in sequence, the criterion being that one reactor must have completed draw prior to another completing fill.

The process of isolation, characterization and utilization of the novel microorganism of this invention is illustrated in the examples which follow. These examples, however, are not intended to limit the scope of the invention except as defined in the appended claims.

EXAMPLE 1

Operation of Sequencing Batch Reactor

Leachate was drawn from the aqueous layer of a settling lagoon at a chemical landfill site. The COD of the leachate ranged from 8000 to 14,000 mg/l. A large percentage of the COD resulted from a high concentration of benzoates and phenols. Less than 1.0% of the COD is attributed to chlorinated organics.

The raw leachate was processed before it was used as feed for the SBRs. The processing procedure consisted of pouring four liters of raw leachate into a five liter Ehrlenmeyer flask. 5.0 ml. of a 10.0N sodium hydroxide solution were added and the flask contents were stirred vigorously for 15 minutes with a magnetic stirring device. The contents of the flask were then poured, one liter at a tie, into a one liter graduated cylinder and allowed to settle for one hour. The clarified supernatant was placed in a large brown glass bottle. The settled solids were carefully poured into a waste drum. The pH of the leachate was adjusted to approximately 7.0 and stored at room temperature under a hood. By raising the pH and aerating the leachate, irons, various salts, and heavy metals were precipitated out of solution in the form of iron base precipitates.

The sequencing batch reactors used in this investigation were initiated with activated sludge which originated from the Niagara Falls POTW municipal activated sludge plant. The first leachate-fed SBR was seeded with a biomass from another SBR operated in accordance with the procedure described in U.S. Pat. 4,511,657. This biomass also contained activated sludge inoculated with microorganisms isolated from a chemical landfill site. The microorganisms were identified as *Pseudomonas cepacia* strain SS3 and *Pseudomonas cepacia* strain H4. *Pseudomonas cepacia* strain SS3 was isolated on 2,6-dichlorotoluene as is sole source of carbon and energy. *Pseudomonas cepacia* strain H4 was isolated on 3-chlorotoluene.

The reactor biomass was split and used to seed two other SBRs. One of the SBRs, designated Reactor I, was fed 75.0 ml. of leachate per day.

Operation of Reactor I was begun 120 days after the start-up of the first leachate-fed SBR, and 76 days after the formation of Reactor I. The color of Reactor I was pale yellow.

The SBR consisted of one liter glass beaker situated atop a magnetic stirring device. A magnetic stir bar was placed on the bottom of each reactor to provide mixing. The reactor contents ere aerated with compressed air which was passed through a diffuser stone located near the bottom of the reactor. Tin foil was placed loosely over the top of the reactor to prevent overflow from excessive foaming.

The Nikon Optiphot Microscope was used for microscopic examination of the biomass.

All pH readings were done on a Fischer Acumet pH meter model 825 MP.

The SBR was operated at room temperature, on a 24 hour cycle divided into the five periods common to sequencing batch reactor operation. They are, in order, FILL, REACT, SETTLE, DRAW, and IDLE.

FILL was the time period when substrate was added to the SBR. The addition of substrate to the reactors consisted of filter sterilizing the required volume of processed leachate in 100 ml. sterile, disposable Nalgene filter units. The filtered leachate was then poured directly into the SBR. The reactor received 75.0 ml. of leachate per day at the outset. The operational volume of the SBR was 750 ml. which resulted in a detention time of 7.5 days. The reactor was supplemented with 10 mg. of $N-NH_4$ and 2 mg. of $P-PO_4$ per 1 per day for nutritional purposes. There was no aeration or mixing during FILL.

The REACT period involved both aeration and mixing. It was 18 hours in length.

During SETTLE, aeration and mixing were stopped and the diffusing stone removed. In addition, microbial growth on the sides of the reactor was scraped loose with a rubber spatula and allowed to settle. The reactor contents were allowed to SETTLE for 5.75 hours.

DRAW consisted of simply pouring off the clarified supernatant from the top of the SBR at the end of SETTLE. The DRAW volume varied due to evaporation of reactor contents and overflow due to foaming. However, the reactors were always drawn down to a volume such that when substrate was added, the total volume in the SBRs would be 750 ml.

IDLE was the time period between the end of DRAW and the beginning of FILL. It was variable, though never more than five minutes. DRAW, IDLE, and FILL lasted approximately fifteen minutes total.

A listing of the standard analysis performed on the SBRs during this investigation is shown below:

| Analysis | Method |
| --- | --- |
| Suspended Solids | Glass Fiber Filter |
| Volatile Suspended Solids | Glass Fiber Filter |
| Sludge Volume Index | 100 ml. Cylinder |

The standard analyses were conducted using the guidelines set forth in *Standard Methods for the Examination of Water and Wastewater*, 15th ed., American Public Health Association, Washington, D.C. (1981). Mixed liquor suspended solids concentrations (MLSS) were determined approximately every other day and the sludge volume index (SVI) was measured once per week. The SVI analyses were performed at the MLSS of the reactors.

COD calculations were performed according to Jirka, A. M. and Carter, M. J., "Micro Semi-Automated Analysis of Surface and Wastewaters for Chemical Oxygen Demand", *Analytical Chemistry*, 47, 1397 (1975). Samples of processed leachate were filtered and refrigerated prior to COD analysis.

Periodically, large volumes of reactor contents were removed for experimental purposes.

The MLSS was considered the primary indicator of the viability of the system. The feed strategy for the SBR was changed at various times during the first few weeks of operation in order to alleviate problems observed in its functioning demonstrated by the MLSS.

Reactor I remained pale yellow in color through day 19. Microscopic examination of the reactor contents showed a fungus-like biomass bearing a high concentration of filaments. The leachate fed to Reactor I at this point was reduced to 50.0 ml. in an attempts to promote a more flocculant microbial population. Detention time was 15 days. The MLSS concentration increased from 4000 to 7000 over the next 20 days. The SBR biomass darkened to a light brown color. Microscopically, the biomass showed flocs present, as well as a higher concentration of protozoa than previously observed. On day 38, leachate addition to Reactor I was once again increased to 100 ml. per day and remained at that level for the duration of the experiment.

EXAMPLE 2

Characterization of Microorganisms

The microorganisms were kept on LB agar plates with 0.1% (v/v) leachate added to prevent the loss of leachate-degradative activities. LB, per liter of water, consists of 10.0 g of tryptone, 5.0 gr. of yeast extract. 5.0 g of sodium chloride, and 1.0 g of glucose. The pH was adjusted to 7.0 with NaOH. After autoclaving, the leachate was added to 0.1% (v/v). For solid media, agar was added to a concentration of 1.5% (v/v).

Methods of microorganism identification followed standard procedures as outlined in *Bergey's Manual* and the *Journal of General Microbiology*.

An experiment to determine if the microorganisms employed the ortho or meta pathway for cleavage of the aromatic ring was performed as outlined in the *Manual of Methods for General Bacteriology*. *Esherichia coli* was used as the negative control.

Growth tests were conducted in 250 ml. Ehrlenmeyer flasks. The inoculant was a turbid solution formed by dispersing approximately one loopful of culture in sterile water. One ml. of inoculant was added to 100 ml. of sterile basal salts medium containing 1.0 mg/ml of the test substrate. Test substrates included 2-chlorobenzoic acid, 3-chlorobenzoic acid, 4-chlorobenzoic acid, and 2,5-dichlorobenzoic acid. Growth on p-hydroxybenzoate was used as a control. After inoculation, the flasks were placed in a 28° C. floor shaker.

Cell density was used as an indication of cell growth. Cell density measurements were taken at 420 nm. using the Bausch and Lomb Spectronic 20. *Pseudomonas putida* strain UNK-1 was isolated from samples of reactor biomass from leachate-fed SBR augmented with

*Pseudomonas cepacia* strain SS3. It was identified as a nonfluorescent *Pseudomonas putida* biovar group B. It is a gram negative, aerobic, polymorphic coccobacili.

All the isolates were tested to determine if they utilized the ortho or meta pathway for cleavage of the aromatic ring, and all were shown to employ the ortho pathway.

The degradation of halogenated aromatic compounds has been shown to occur only via the ortho pathway. The meta pathway is unproductive for the degradation of haloaromatics. Therefore, all of the microorganisms might possess the potential to catabolize haloaromatic compounds.

Growth tests revealed that *Pseudomonas putida* strain UNK-1 was the only isolate to utilize any of the test substrates as its sole source of carbon and energy under the experimental conditions. This microorganism readily metabolized 2-chlorobenzoic acid resulting in a rapid increase in cell density. All of the isolates were able to utilize p-hydroxybenzoate as their sole source of carbon and energy. Therefore, they were capable of metabolizing aromatic compounds. However, with the exception of strain UNK-1, they were not able to grow on any of the chlorobenzoates as tested here. The presence of the chloride substituent was assumed to be the inhibiting factor suggesting that enzyme systems in these isolates were not capable of attacking the chlorinated aromatic acids. *Pseudomonas capacia* strains SS3 and H4 have shown the ability to metabolize 2-chlorobenzoic acid and 4-chlorobenzoic acid by growth on solid medium. It is important to note that growth in liquid culture was not observed. If microorganisms cannot metabolize haloaromatics in a liquid environment, they would not be useful for the bioaugmentation of a leachate-fed SBR.

EXAMPLE 3

Isolation of Plasmids from Microorganisms

Prior to plasmid extraction, all microorganisms were grown for 20 to 24 hours at 27 degrees Celsium on LB plus (0.1% (v/v) leachate agar plates. The presence of the leachate in the growth medium applied selective pressure on the microorganisms for the retention of their plasmids.

The plasmid extraction procedure was that of Hanson, J. B. and Olsen, R. H., "Isolation of Large Bacterial Plasmids and Characterization of the P2 Incompatibility Group Plasmids pMG1 and pMG5", *Journal of Bacteriology*, 135, 277 (1978). Stock solutions are listed in Table 2 and plasmid isolation is listed in Table 3.

TABLE 2

| Solution | Contents |
|---|---|
| TE Buffer | 0.5M tris-(hydroxymethyl)aminomethane (Tris) (pH 8.0) |
| | 0.2M disodiumethylenediaminetetraacetate (Na2EDTA) (pH 8.0) |
| TES Buffer | 0.05M Tris |
| | 0.05M sodium chloride |
| | 5.0 mM Na2EDTA |
| Tris/Sucrose Buffer | 25% (w/v) Sucrose |
| | 0.05M Tris |
| Na2EDTA Solution | 0.25M Na2EDTA (pH 8.0) |
| SDS | 20% (w/v) sodium lauryl sulfate in TE |
| Alkaline Denaturation Solution | 3.0N sodium hydroxide (NaOH) |
| Neutralizing Solution | 2.0M Tris (pH 7.0) |
| High Salt | 5.0M sodium chloride (NaCl) |

TABLE 2-continued

| Solution | Contents |
|---|---|
| Solution | |

TABLE 3

| Step | Operation |
|---|---|
| Cell Growth | 20 to 24 hours on LB plus 0.1% (v/v) leachate agar plates |
| Cell Lysis | Washed cells resuspended in 25% Sucrose Buffer with 100 ug. of mutanolysin |
| | Refrigerate in ice bath for one hour |
| | 0.25M Na2EDTA (pH 8.0) added |
| | SDS added to 4.0% (w/v) |
| | Intermittent heat pulses at 55° C in water bath |
| Alkaline Denaturation | 3.0N NaOH added to raise pH to 12.1 to 12.3 |
| Neutralization | 2.0M Tris (pH 7.0) added to reduce pH to 8.5 to 9.0 |
| Precipitation of membrane-chromosomal complexes | SDS added to 4.0% (w/v) and 5.0M NaCl added to 1.0M |
| | Refrigerate in ice bath overnight |
| Concentration of Polyethylene glycol added to 10% (w/v) plasmid DNA | Refrigerate in ice bath overnight |
| | Centrifugation at 2500 RPM for 5 minutes and resuspend in 0.2 ml. of TES buffer |

Centrifuges used in plasmid isolation included the Fisher Micro-Centrifuge Model 235B for plasmid minipreps. Larger preps were centrifuged in 50.0 ml. propylene centrifuge tubes using the Sorvall Superspeed RC2-B Automatic Refrigerated Centrifuge.

Cesium-chloride equilibrium density gradients of the crude plasmid extracts were performed in the Beckman Model L3-50 Ultracentrifuge. Following ultracentrifugation, purified plasmid DNA wa dialyzed against a buffer which consisted of 10.0 mM tris, 15.0 mM NaCl, and 2.0 mM EDTA in water. pH was 8.0.

Plasmid DNA was subjected to electrophoresis. A Tris-borate gel buffer was used. It consisted of 10.8 g/l of Tris, 5.5 g/l of borate, and 4.0 ml. of a .05M Na2EDTA solution (pH 8.0). Large gels were run on the BRL Horizontal Gel Electrophoresis System Model H3 in 0.7% (w/v) agarose gels at 80 volts for 3 hours. Mini gels were performed on the Hoefer Scientific HE 33 "Minnie" Horizontal Submarine Unit in 1.0% (w/v) agarose gels at 140 volts for 45 minutes. The Heath Zenith Regulated H.V. Power Supply Model SP-2717A was used with both units. The tracking dye was 50% glycerol, 0.07% bromophenol blue, and 50.0 mM of EDTA in water.

Gels were strained with ethidium bromide, 0.1 ug/ml in Tris-borate buffer, in the dark for one half hour.

All gels were photographed using an Ultra Violet Products Chromato-Vue transilluminatr Model TM-36 with Polaroid MP-4 Land Camera 44-01 equipped with a red filter. Mini-survey lysis (HOL II), a small, quick assay, and the multiplate procedures were employed for plasmid extraction. HOL II is used in association with gel electrophoresis for rapid initial examination of bacteria to determine the presence or absence of plasmids. The multiplate Hansen and Olsen method (HO) is used when large amounts of plasmid DNA are to be extracted. The microorganisms were examined for plasmid presence using both Hansen and Olsen procedures.

*Pseudomonas putida* strain UNK-1 consistently yielded two large plasmids using the HOL II mini-survey assay. HOL II eas unsuccessful with the other microorganisms. However, proportionately increasing input volumes allowed HOL II to e used in multiplate plasmid isolations. This technique worked well with polyethylene glycol to concentrate the p-DNA rather than 100% ethanol. The microorganisms received double the prescribed reagent concentrations. From ten plates of each culture, this procedure yielded positive results with *Pseudomonas cepacia* strain H4 and *Pseudomonas putida* strain UNK-1, but not *Pseudomonas cepacia* strain SS3.

The Hansen and Olsen multiplate procedure, in association with cesium-chloride equilibrium density gradient centrifugation, proved more effective in isolating plasmids from the isolates. The results were consistent and reproducible. The procedure was modified slightly to accommodate the nature of the microorganisms. The isolates were resistant to lysing possibly due to the fact that they originated from such an extreme environment. Therefore, the lysis step was extended from five to sixty minutes to provide for more complete lysing of the cell suspension. Also, mutanolysin, instead of lysozyme, was used as the lysing agent.

The results using the HO procedure showed that strain H4 contained a large plasmid, while strains SS3 and UNK-1 each harbored two large plasmids. Relative size comparisons can be made within the representation o a PAGE gel. The plasmid in strain H4, the larger plasmid in strain UNK-1, and the smaller plasmid in strain SS3 all were similar in size. Strain UNK-1 harbored the smallest plasmid. Previously, three large plasmids were found in strain SS3 using the Hansen and Olsen procedure and it was demonstrated that the chloroaromatic degradative ability of strain SS3 was ransmissible via these plasmids. These plasmids were identified as pRo 4.7, pRo 31 and pRo 54 in U.S. Pat. No. 4,447,570.

The fact that these isolates possessed plasmids suggested that the plasmids coded for the degradation of complex organic compounds. They were obtained from the landfill site, used for the disposal of chlorinated organic wastes, and an SBR fed leachate. Plasmids have been shown to code for the dissimilation of complex organic compounds to simple organic acids which can be used in the central pathways of the microorganism. They can spread among indigenous populations via recombination, conjugation, or transformation thus serving the evolutionary process via the conferring of genetic diversity. They may have evolved as a survival mechanism for microorganisms in extreme environments. Under conditions of high localized concentrations of toxic substances, as existed at the landfill and in the leachate-fed SBR, plasmid encoded functions are capable of detoxifying the environment. The plasmids in the present microorganisms may have evolved for this purpose.

EXAMPLE 4

Chloride Release Tests on Microorganisms

Pure cultures of the microorganisms of Example 2 were isolated on agar plates of basal salts medium containing 0.1% (w/v) of either 2-chlorobenzoic acid (2Cba) or 2,5-dichlorobenzoic acid (2,5dCba). The microorganisms were maintained on TNA plus 0.1% (v/v) HPL agar plates.

The chloride ion concentration readings were done using the Fisher Acumet 25 meter using an Orion solid-state Chloride Selective electrode model 94-17B and the Orion Double Junction reference electrode model 90-02.

The test compounds were 2-chlorobenzoic acid (2Cba), 3-chlorobenzoic acid (3Cba), 4-chlorobenzoic acid (4Cba), 2,5-dichlorobenzoic acid (2,5dCba), 2,6-dichlorobenzoic acid (2,6dCba), and m-chlorotoluene (mCT).

The inoculum for each experiment was prepared by scraping approximately two loopfuls of selected culture from an agar plate and dispersing it into 100 ml. of growth medium in a 250 ml. Ehrlenmeyer flask. The growth medium consisted of TNB plus leachate at a concentration of 0.1% (v/v). The flask was then placed in a 28 degree Celsius floor shaker for 20 to 24 hours.

At the end of this period, the optical density of a 1:10 dilution was measured at 425 nm. on the Bausch and Lomb Spectronic 20. A volume of culture was then used to inoculate the chloride release flasks such that the optical density in the flask at 425 nm. would be 1.0, which resulted in a cell density of approximately ten to the eighth cells/ml.

The basal salts media (BSM) for the chloride release experiments consisted of, per liter of deionized water, 5.8 g of $K_2HPO_4$, 4.5 g. of $KH_2PO_4$, 2.0 g. of $(NH_4)_2SO_4$, 0.16 g. of $MgCl_2.2H_2O$, 20.0 mg. of $CaCl_2$, 2.0 mg. of $NaMgO_4$, 1.0 mg. of $FeSO_4$, and 1.0 mg. of $MnCl_2$.

Chloride release experiments were conducted in 250 ml. Ehrlenmeyer flasks. 40.0 ml. of BSM was added to each flask and a sponge or cotton plug was inserted into the mouth. The flasks and contents were sterilized. The test compound was added at a concentration of 1.0 mg/ml. When two test compounds were present in the same flask, their concentrations were 0.5 mg/ml respectively. The final volume in the chloride release flasks was 60.0 ml. Inoculate volume was equal to one third of the final flask volume. There were three control flasks. One contained BSM only, the second contained BSM with the test compound, and the final flask contained BSM with reactor biomass only. All chloride release flasks were kept in the dark in a 30° incubator.

The chloride release flasks were removed periodically for sampling. All chloride ion concentration readings were done on the Fisher Acumet 825 meter using an Orion solid-state Chloride Selective electrode model 94-17B and the Orion Double Junction reference electrode model 90-02.

Measurements were performed by extracting 3.0 ml. of sample from each flask and mixing it with 27.0 ml. of distilled water for a 1:10 dilution. Next, 0.5 ml. of deionizing solution was added to each sample. The sample was then placed in a 50.0 ml. beaker and mixed with a magnetic stirring device. The electrodes were introduced into the solution and the readings were recorded after they had stabilized which normally required two to three minutes. The chloride ion concentration readings were multiplied ten times for the actual chloride ion concentration. The amount of chloride released was calculated as the percentage of the theoretical total amount of chloride present in the test compound. The first readings were taken immediately following inoculation for a day zero reading.

Three sets of chloride release experiments were conducted. Each lasted approximately three weeks.

The microorganisms were tested for the compound they were isolated on, either 2Cba, or 2,5dCba. The results of this initial chloride release study revealed that the isolate designated *Pseudomonas putida* strain UNK-1 released 60% of the chloride from 2Cba in two days. All the chloride was released in six days. None of the other pure cultures showed any activity toward 2Cba. No chloride release was observed in any of the flasks containing 2,5dCba as the test compound.

The leachate-fed sequencing batch reactor, bioaugmented with strain SS3 appeared to have developed a microorganism, designated *Pseudomonas putida* strain UNK-1, with the ability to completely degrade 2Cba with subsequent release of chloride.

The follow-up to this experiment consisted of combining 2Cba with another chlorinated aromatic compound, 3Cba, 4Cba, 2,5dCb, 2,6dCba, or mCT in chloride release flasks inoculated with strain UNK-1. It was hoped that 2Cba would induce the necessary enzymes from strain UNK-1 for the degradation of the target compound. The analogue enrichment technique suggests that biodegradation in the presence of a structurally analogous compound will increase the rate of degradation of the target substance. Each test substrate was tested separately and in combination with 2Cba.

The results of the follow-up chloride release experiment were in agreement with the previous experiment. Strain UNK-1 released all the chloride with 2Cba within 3 days and showed no activity toward any of the other test compounds as its sole source of carbon and energy. Chloride release was observed in the flask containing two test compounds when 2Cba was in combination with 4Cba, 2,5dCba, and mCT. Within three days, half of the chloride in these flasks had been released. This appeared to indicate complete utilization of 2Cba by strain UNK-1. The increase in chloride ion concentration thereafter may have been due to evaporation losses, or it could have represented the initiation of chloride release from the other test compound. Only 40% of the chloride was released in the flask containing 2Cba with 2,6dCba.

When 2Cba was in combination with 3Cba, no chloride was released. In all other flasks, the activity towards 2Cba seemed to have been unaffected by the presence of another substrate. However, 3Cba appeared to inhibit the degradation of 2Cba by strain UNK-1.

The chloride release experiments were meant to demonstrate complete utilization of the test compound as indicated by dehalogenation. Dehalogenation has been shown to occur following ring cleavage, in chlorinated benzoic acids. Partial degradation may have occurred in flasks where no chloride release was observed. A mixed substrate or mixed culture environment may have been necessary for some microorganisms to cometabolize the target compound and demonstrate chloride release.

Although various embodiments of this invention have been shown and described in the specification, this invention is intended to be construed liberally and not limited by any specific embodiments as will be readily appreciated by those skilled in the art. It is to be understood, therefore, that the appended claims are intended to cover all modifications and variations which are within the spirit and scope of the present invention.

What is claimed is:

1. A process for biologically treating chemical process wastewater and chemical waste landfill leachate in a sequencing batch reactor system to degrade the recalcitrant organic compounds contained therein comprising the steps of
   (a) establishing an activated sludge in the sequencing batch reactor containing an aqueous medium having both recalcitrant and non-recalcitrant organic compounds, said activated sludge being capable of metabolizing the non-calcitrant components of the wastewater or leachate;
   (b) augmenting the activated sludge with a microorganism capable of metabolizing the recalcitrant organic compounds in the aqueous medium, said microorganism selected from the group consisting of *Pseudomonas putida* strain UNK-1 having accession number ATCC 68832, mutants thereof, and mixtures of said strain and mutants thereof, where said microorganism is capable of degrading haloaromatic compounds in an aqueous medium; and
   (c) disposing of the waste effluent and waste sludge produced in the reactor.

2. The process of claim 1 wherein the recalcitrant compounds are chlorinated aromatic compounds.

3. The process of claim 2 wherein the chlorinated aromatic compounds are chlorobenzoic acids.

4. A process for the microbial degradation of toxic halogenated organic chemical waste, which comprises applying to the locus of said halogenated organic chemical waste an aqueous medium containing a microorganism selected from the group consisting of *Pseudomonas putida* strain UNK-1 having accession number ATCC 68832mutants thereof, and mixtures of said strain and mutants thereof, where said microorganism is capable of degrading haloaromatic compounds in said aqueous medium.

5. The process of claim 4 wherein said locus is aerated soil wherein the soil is further combined with a nutrient.

6. The process of claim 5 wherein the locus to be degraded is a landfill.

7. The process of claim 5 wherein the locus to be degraded is a leachate removed from the landfill.

8. The process of claim 4 wherein the halogenated organic chemical waste is predominantly chlorinated aromatic chemicals.

9. The process of claim 8 wherein the metabolic pathway for degradation includes one or more chlorobenzoic acid compounds.

* * * * *